(12) United States Patent
Kaltenbach, III et al.

(10) Patent No.: US 6,528,681 B2
(45) Date of Patent: Mar. 4, 2003

(54) HALOGENATED TRIPHENYLETHYLENE DERIVATIVES AS SELECTIVE ESTROGEN RECEPTOR MODULATORS

(75) Inventors: Robert F. Kaltenbach, III, Wilmington, DE (US); George L. Trainor, Wilmington, DE (US)

(73) Assignee: Bristol-Meyers Squibb Pharma Company, Princeton, NJ (US)

( * ) Notice: Subject to any disclaimer, the term of this patent is extended or adjusted under 35 U.S.C. 154(b) by 24 days.

(21) Appl. No.: 09/824,868

(22) Filed: Apr. 3, 2001

(65) Prior Publication Data

US 2002/0013297 A1 Jan. 31, 2002

Related U.S. Application Data

(60) Provisional application No. 60/194,579, filed on Apr. 5, 2000.

(51) Int. Cl.[7] .............................................. C07C 63/33
(52) U.S. Cl. ...................... 562/491; 560/101; 514/570
(58) Field of Search ........................ 514/570; 562/491; 560/101

(56) References Cited

U.S. PATENT DOCUMENTS 5,681,835 A    10/1997   Willson

FOREIGN PATENT DOCUMENTS

WO    99/08682    2/1999

OTHER PUBLICATIONS

Kauffman et al., JPET 280:146–153 (1997).
Wagner et al., Proc. Natl. Acad. Sci. Usa 93:8739–8744 (1996).
Tonetti and Jordan, Anti–Cancer Drugs 6:498–507 (1995).
McDonnell et al. Mol. Endocrinol. 9:659–669 (1995).
Tzukerman et al. Mol Endocrinol. 8:21–30 (1994).
Kedar et al. Lancet 353:1318–1321 (1994).
J. Med. Chem. 37:1550–1552 (1994).
Black et al., J. Clin. Invest 93:63–69 (1994).
Beekman et al., Molecular Endocrinology 7:1266–1274 (1993).
Eaker et al. Circulation 88:1999–2009 (1993).
Parker, Breast Cancer Res. Treat. 26:131–137 (1993).
Chow et al., J. Clin. Invest. 89:74–78 (1992).
Love et al., New Engl. J. Med. 326:852–856 (1992).
Love et al., Ann. Intern.Med. 115:860–864 (1991).
O'Malley et al, Hormone Research 47:1–26 (1991).
Jordan and Murphy, Endocrine Reviews 11:578–610 (1990).
Tasset et al, Cell 62:1177–1181 (1990).
Skehan et al., New Colorimetric Cyctotoxicity Assay For Anticancer Drug Screening, J. Nat'l. Cancer Inst. 82:1107–1112 (1990).
Tora et al. Cell 59:471–487 (1989).
Robinson et al., Cancer Rese. 49:1758–1762 (1989).
Evans, Science 240:889–895 (1988).
R. B. Miller et al, J. Org. Chem. 50:2121–2123 (1985).

*Primary Examiner*—Paul J. Killos

(57) ABSTRACT

The present invention describes novel halogenated triphenylethylene derivatives, or pharmaceutically acceptable prodrug or salt forms thereof, as selective estrogen receptor modulators for the treatment of and/or prevention of breast, uterine, ovarian, prostrate and colon cancer, osteoporosis, cardiovascular disease, and benign proliferative disorders, as well as methods for making the compounds and pharmaceutical compositions of this invention.

6 Claims, 1 Drawing Sheet

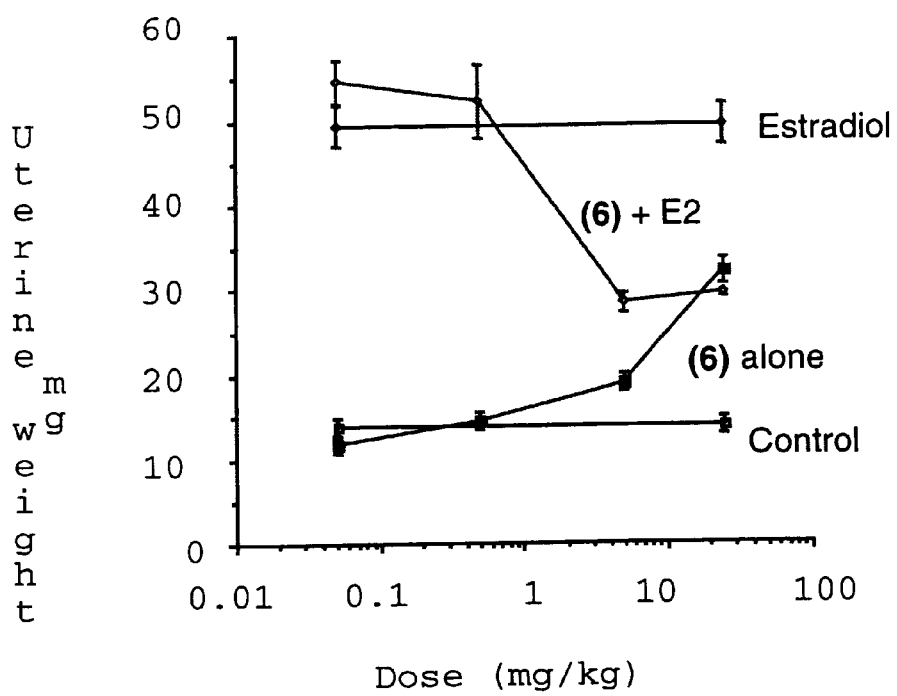
Figure 1: Estrogen caused an increase in the uterine weight of ovariectomized mice. Compound (6), 3-[4-[1-(4-fluorophenyl)-2-phenyl-but-1-enyl]phenyl]acrylic acid, produced a dose-related inhibition when co-administered.

HALOGENATED TRIPHENYLETHYLENE DERIVATIVES AS SELECTIVE ESTROGEN RECEPTOR MODULATORS

FIELD OF THE INVENTION

This invention pertains to novel halogenated triphenylethylene derivatives as selective estrogen receptor modulators for the treatment and/or prevention of breast, uterine, ovarian, prostrate and colon cancer, osteoporosis, cardiovascular disease, and benign proliferative disorders, as well as methods for making the compounds and pharmaceutical compositions of this invention.

BACKGROUND OF THE INVENTION

Approximately 180,000 women are diagnosed with breast cancer each year in the United States. Most of these women are cured of their disease by surgery and local radiotherapy. However, nearly 60,000 women go on to develop metastatic breast cancer each year, and 45,000 of these patients eventually die from their malignancies. While metastatic breast cancer is rarely curable, it is treatable with modern pharmaceuticals that prolong patient survival and reduce the morbidity associated with metastatic lesions. Foremost among these therapies are hormonal manipulations that include selective estrogen receptor modifiers (SERMs). SERMs are small ligands of the estrogen receptor that are capable of inducing a wide variety of conformational changes in the receptor and thereby eliciting a variety of distinct biological profiles. SERMs not only affect the growth of breast cancer tissue but also influence other physiological processes. The most widely used SERM in breast cancer is tamoxifen, which is a partial estrogen receptor agonist/antagonist that produces objective responses in approximately 50% of the patients. Unfortunately, 100% of patients who take tamoxifen eventually relapse with tamoxifen-resistant tumors. Approximately 50% of the patients that fail tamoxifen treatment will respond to a subsequent hormonal manipulation therapy such as castration, aromatase inhibitors, or other SERMs. The second line therapies for hormonal manipulation therapy of metastatic breast cancer represent a substantial unmet need because no single agent has become the treatment of choice for patients who fail tamoxifen therapy. The ideal agent would be a medication that induces regression of metastatic breast cancer lesions in women who have previously responded to tamoxifen therapy. The compounds most apt to meet these requirements will likely be second generation SERMs such as 3-[4[(1,2-diphenyl-but-1-enyl)-phenyl]-acrylic acid, or a compound of the present invention. The present invention is structurally related to, but patentably distinct from, the compound 3-[4[(1,2-diphenyl-but-1-enyl)-phenyl]-acrylic acid, which is described in U.S. Pat. No. 5,681,835.

SERMs modulate the proliferation of uterine tissue, skeletal bone density, and cardiovascular health, including plasma cholesterol levels. In general, estrogen stimulates breast and endometrial tissue proliferation, enhances bone density, and lowers plasma cholesterol. Many SERMs are bifunctional in that they antagonize some of these functions while stimulating others. For example, tamoxifen, which is a partial agonist/antagonist at the estrogen receptor inhibits estrogen-induced breast cancer cell proliferation but stimulates endometrial tissue growth and prevents bone loss. Estrogens are an important class of steroidal hormones that stimulate the development and maintenance of fundamental sexual characteristics in humans. In the past, estrogens have been found useful in the treatment of certain medical conditions and diseases. For example estradiol, a steroid hormone produced by the ovary, is useful in the treatment of osteoporosis, cardiovascular disease, premenstrual syndrome, vasomotor symptoms associated with menopause, atrophic vaginitis, Kraurosis vulvae, female hypogonadism, primary ovarian failure, excessive hair growth and prostatic cancer.

Hormone replacement therapy (HRT) with estrogen has been determined to be a clinically effective treatment for osteoporosis in post-menopausal women. However, less than 15% of eligible women are currently prescribed HRT despite clinical trials that have demonstrated a 50% reduction in hip fractures and a 30% reduction in cardiovascular disease. Non-compliance arises from patient and physician concerns over the two fold increased risk of endometrial cancer observed with HRT employing estrogen alone as well as the association between estrogen therapy and breast cancer. Although unproven in the clinic, this suspected risk for breast cancer has led to HRT being contraindicated in a significant percentage of post-menopausal women. Co-therapy with progestins has been shown to protect the uterus against cancer while maintaining the osteoprotective effects of the estrogen, however the progestin introduces other side effects such as withdrawal bleeding, breast pain and mood swings.

In light of the more serious side effects associated with estrogen therapy, including myocardial infarction, thromboembolism, cerebrovascular disease, and endometrial carcinoma, a significant amount of research has been carried out to identify effective nonsteroidal estrogen and antiestrogenic compounds. In general, such compounds may be characterized as both estrogenic and antiestrogenic because, while they all bind to the estrogen receptor, they may induce an estrogenic or antiestrogenic effect depending upon the location of the receptor. In the past, it has been postulated that the binding of various nonsteroidal estrogen and antiestrogenic compounds to the estrogen receptor was due to the presence of a common pharmacophore (shown below in Scheme A), which was recurrent in the chemical structures of these compounds.

Scheme A

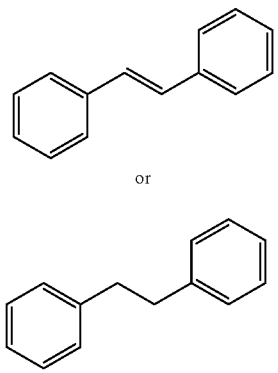

This pharmacophore later became the structural backbone around which nonsteroidal estrogen and antiestrogenic compounds were constructed. Its presence in the constructs of various compounds such as hexestrol, tamoxifen, chroman, triphenylethylene, DES, clomiphene, centchroman, nafoxidene, trioxifene, toremifene, zindoxifene, raloxifene, droloxifene, DABP, TAT-59 and other structurally related compounds has become accepted in the art as the molecular key to estrogen receptor binding specificity.

Estrogen has also been shown to function as a mitogen in estrogen-receptor (ER) positive breast cancer cells. Thus, treatment regiments which include antiestrogens, synthetic compounds which oppose, the actions of estrogen have been effective clinically in halting or delaying the progression of the disease (Jordan and Murphy, Endocrine Reviews 11:578–610 1990); Parker, Breast Cancer Res. Treat. 26:131–137 (1993)). The availability of these synthetic ER modulators and subsequent dissection of their mechanism(s) of action have provided useful insights into ER action.

The human estrogen receptor (ER) is a member of the nuclear receptor superfamily of transcription factors (Evans, Science 240:889–895 (1988)). In the absence of hormone, it resides in the nucleus of target cells in a transcriptionally inactive state. Upon binding ligand, ER undergoes a conformational change initiating a cascade of events leading ultimately to its association with specific regulatory regions within target genes (O'Malley et al., Hormone Research 47:1–26 (1991)). The ensuing effect on transcription is influenced by the cell and promoter context of the DNA-bound receptor (Tora et al. Cell 59:471–487 (1989) (Tasset et al., Cell 62:1177–1181 (1990); McDonnell et all Mol. Endocrinol. 9:659–669 (1995); Tzukerman et al. Mol. Endocrinol. 8:21–30 (1994)). It is in this manner that the physiological ER-agonist, extradiol, exerts its biological activity in the reproductive, skeletal and cardiovascular systems (Clark and Peck, Female Sex Steroids:Receptors and Function (eds) Monographs Springer-Verlag, New York (1979); Chow et al., J. Clin. Invest.89:74–78 (1992); Eaker et al. Circulation 88:1999–2009 (1993)).

One of the most studied compounds in this regard is tamoxifen (TAM), (Z)1,2-diphenyl-1-[4-[2-(dimethylamino)ethoxy]phenyl]-1-butene, (Jordan and Murphy, Endocrine Reviews 11:578–610 (1990)), which is a triphenylethylene derivative. Tamoxifen functions as an antagonist in most ER-positive tumors of the breast and ovum, but displays a paradoxical agonist activity in bone and the cardiovascular system and partial agonist activity in the uterus (Kedar et al. Lancet 343:1318–1321 (1994); Love et al., New Engl. J. Med. 326:852–856 (1992); Love et al., Ann. Intern. Med. 115:860–864 (1991)). Thus, the agonist/antagonist activity of the ER-tamoxifen complex is influenced by cell context. This important observation is in apparent contradiction to longstanding models that hold that ER only exists in the cell in an active or an inactive state (Clark and Peck, Female Sex Steroids:Receptors and Functions (eds) Monographs on Endocrinology, Springer-Verlag, New York (1979)). It indicates instead that different ligands acting through the same receptor can manifest different biologies in different cells. Definition of the mechanism of this selectivity is likely to advance the understanding of processes such as tamoxifen resistance, observed in most ER-containing breast cancers, where abnormalities in ER-signaling are implicated (Tonetti and Jordan, Anti-Cancer Drugs 6:498–507 (1995)).

Tamoxifen, as well as a structurally similar compound known as raloxifene have been developed for the treatment and/or prevention of osteoporosis, cardiovascular disease and breast cancer in addition to the treatment and/or prevention of a variety of other disease states. Both compounds have been shown to exhibit an osteoprotective effect on bone mineral density combined with a positive effect on plasma cholesterol levels and a greatly reduced incidence of breast and uterine cancer. Unfortunately, tamoxifen and raloxifene both have unacceptable levels of life-threatening side effects such as endometrial cancer and hepatocellular carcinoma.

The likely mechanism for the cell selective agonist/antagonist activity of tamoxifen has been determined using an in vitro approach (Tora et al., Cell 59:477487 (1989); Tasset et al., Cell 62:1177–1187 (1990); McDonnell et al., Mol. Endocrinol. 9:659–669 (1995); Tzukerman et al., Mol. Endocrinol. 8:21–30 (1994)). Importantly, it has been shown that tamoxifen induces a conformational change within ER which is distinct from that induced by estradiol (McDonnell et al., Mol. Endocrinol. 9:659–669 (1995); (Beekman et al., Molecular Endocrinology 7:1266–1274 (1993)). Furthermore, determination of the sequences within ER required for transcriptional activity indicate how these specific ligand-receptor complexes are differentially recognized by the cellular transcriptional machinery. Specifically, it has been shown that ER contains two activation domains, AF-1 (Activation Function-1) and AF-2, which permit its interaction with the transcription apparatus. The relative contribution of these AFs to overall ER efficacy differs from cell to cell (Tora et al., Cell 59:477–487 (1989); McDonnell et al., Mol. Endocrinol. 9@65-9-669 (1995); Tzukerman et al., Mol. Endocrinol. 8:21–30 (1994)). Estradiol was determined to function as both an AF-1 and an AF-2 agonist, in that it exhibited maximal activity regardless of which AF was dominant in a given cellular environment. Tamoxifen, on the other hand, functions as an AF-2 antagonist, inhibiting ER activity in cells where AF-2 is required or is the dominant activator (Tora et al., Cell 59:477–487 (1989); McDonnell et al., Mol. Endocrinol. 9:659–669 (1995); Tzukerman et al., Mol. Endocrinol. 8:21–30 (1994)). Conversely, tamoxifen functions as an agonist when AF-1 alone is required (McDonnell et al., Mol. Endocrinol. 9:659–669 (1995); Tzukerman et al., Mol. Endocrinol. 8:21–30 (1994)). Subsequently, based on their relative AF-1/AF-2 activity, four mechanistically distinct groups of ER-modulators were defined; full agonists (i.e. estradiol), two distinct classes of partial agonists, represented by tamoxifen and raloxifene, and the pure antagonists, of which ICI182,780 is a representative member (McDonnell et al., Mol. Endocrinol. 9:659–669 (1995); Tzukerman et al., Mol. Endocrinol. 8:21–30 (1994)). These results provide a mechanistic explanation for the observed differences in the biological activities of some ER-modulators and indicate that the mechanism by which ER operates in different tissues is not identical.

Interestingly, the agonist activity exhibited by ER-modulators, such as estrogen and tamoxifen, in these in vitro systems reflects their activity in the reproductive tracts of whole animals. This correlation does not extend to bone, however, where estradiol, tamoxifen and raloxifene, which display different degrees of AF-1/AF-2 agonist activity, all effectively protect against bone loss in the ovariectomized rat model. Thus, with the exception of the steroidal pure antiestrogens (ie, ICI182,780), all known classes of ER modulators appear to protect against bone loss in humans and relevant animal models, while they display different degrees of estrogenic activity in other tissues (Chow et al., J. Clin. Invest. 89:74–78 (1992); Love et al., New Engl. J. Med. 326:852–856 (1992); Draper et al., Biochemical Markers of Bone and Lipid Metabolism in Healthy Postmenopausal Women. In C. Christiansen and B. Biis (eds) Proceedings 1993. Fourth International Symposium on Osteoporosis and Consensus Development Conference, Handelstrykkeriet, Aalborg; Wagner et al., Proc. Natl. Acad. Sci. USA 93:8739–8744 (1996); Black et al., J. Clin. Invest 93:63–69 (1994)).

Accordingly, it would be advantageous to develop a series of non-steroidal compounds that retain beneficial characteristics such as osteoprotective activity while minimizing any undesirable side effects. While it is presently accepted that the pharmacophore backbone mentioned above is responsible for estrogen receptor binding specificity, it has now been discovered that certain novel estrogen binding ligands can be constructed as set forth herein which incorporate particular moieties onto such pharmacophore-based compounds, thereby maximizing beneficial characteristics such as osteoprotective function while minimizing undesirable characteristics such as an increased risk of cancer.

SUMMARY OF THE INVENTION

The present invention describes a novel class of compounds represented by Formula (I):

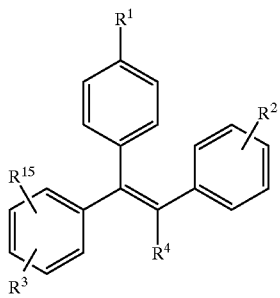

Formula (I)

or pharmaceutically acceptable prodrug or salt forms thereof, wherein $R^1$–$R^{15}$ are defined below, which are selective estrogen receptor modulators.

It is another object of this invention to provide a novel method of treating and/or preventing breast, uterine, ovarian, prostrate and colon cancer, osteoporosis, cardiovascular disease, benign proliferative disorders or other disease states by administering a therapeutically effective amount of one or more of these compounds or a pharmaceutically acceptable prodrug or salt form thereof.

BRIEF DESCRIPTION OF THE DRAWING

FIG. 1: Shows a dose-related inhibition of estrogen-stimulated mouse uterine weight.

DETAILED DESCRIPTION OF THE INVENTION

The invention pertains to novel halogenated triphenylethylene derivatives as selective estrogen receptor modulators for the treatment and/or prevention of breast, uterine, ovarian, prostrate and colon cancer, osteoporosis, cardiovascular disease, benign proliferative disorders and other disease states, as well as methods for making the same, and their application in treating a variety of disease states.

The present invention, in a first embodiment, describes a novel compound of Formula (I):

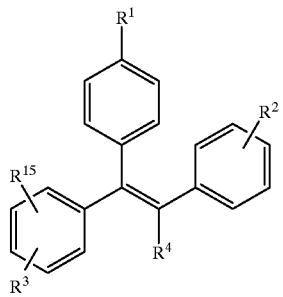

Formula (I)

or a stereoisomer, prodrug, or pharmaceutically acceptable salt form thereof, wherein:

$R^1$ is $(CH_2)_n CR^5=CR^6R^7$,;

$R^2$ is H;

$R^3$ is selected from the group: F, Cl, BR, and I;

$R^4$ is selected from the group: CN, $NO_2$, $CH_3$, $CH_2CH_3$, $CH_2CH_2Y$ and Y;

$R^5$ and $R^6$ are independently at each occurrence selected from the group: H, O, OH, $C_{1-4}$alkyl, $C_{2-4}$alkenyl, $C_{2-4}$ alkynyl, $XC_{1-3}$alkyl, $XC_{2-4}$ alkenyl, $XC_{2-4}$ alkynyl and Y;

$R^7$ is independently at each occurrence selected from the group: $NH_2$, CN, O, OH, $C_{1-4}$ alkyl-OH, $C(O)O(CH_3)$, $C(O)NR^{10}R^{11}$, $C(O)NR^{12}R^{13}$, $C_{1-4}$ alkyl-$NR^{10}R^{11}$, $C(O)R^{12}$, $C(O)OR^{12}$, $C(O)NR^{12}OR^{13}$, $C(O)NHC(O)R^{12}$, $C(O)NHCH_2R^{12}$, $C(NH_2)$ $(NOR^{12})$, $S(O)R^{12}$, $S(O)$ $(O)(OR^{12})$, $S(O)(O)(NHCO_2R^{12})$ $PO_3R^{12}$, $P(O)(NR^{12}R^{13})$ $(NR^{12}R^{13})$, $P(O)$ $(NR^{12}R^{13})(OR^{14})$, $CONR^{12}(CH_2)_qOCH_3$, $CONR^{12}(CH_2)_qNR^8R^9$, and oxadiazole substituted with $CH_3$;

$R^8$ and $R^9$ are independently at each occurrence selected from the group: $C_{1-7}$ alkyl, $C_{3-7}$ cycloalkyl, O—$C_{1-7}$ alkyl, $C_{1-7}$ alkyl-Y, and phenyl;

$R^{10}$ and $R^{11}$ are independently $CH_3$ or $C_2H_5$, or taken together form a morpholino group bonded via its nitrogen atom;

$R^{12}$ and $R^{13}$ and $R^{14}$ are independently at each occurrence selected from the group: H, $C_{1-2}$ alkyl, $C_{2-12}$ alkenyl, $C_{2-12}$ alkynyl, O—$C_{1-2}$ alkyl, O—$C_{2-12}$ alkenyl, O—$C_{2-12}$ alkynyl, $C_{3-7}$ cycloalkyl, $C_{3-7}$ cycloalkenyl, linear and cyclic heteroalkyl, aryl, heteroaryl, and Y;

$R^{15}$ is selected from the group: H and F;

X is selected from the group: O and S;

Y is selected from the group: F, Cl, Br, and I;

n is selected from: 0, 1, and 2;

m is selected from: 1 and 2;

p is selected from: 1, 2, 3, and 4; and q is selected from: 1, 2, 3, 4, 5, 6, 7, 8, 9, 10, 11, and 12.

A preferred embodiment, the present invention provides a novel compound of Formula (I), wherein:

$R^1$ is $(CH_2)_n CR^5=CR^6R^7$;

$R^2$ is H;

$R^3$ is F;

$R^4$ is $CH_3$;

$R^5$ is H;

$R^6$ is O; and $R^{15}$ is selected from the group: H and F.

A more preferred embodiment, the present invention provides a novel compound of Formula (I), wherein:

$R^1$ is $CR^5=CR^6R^7$ $R^2$ is H;

$R^3$ is F;

$R^4$ is $CH_3$;

$R^5$ is H;

$R^6$ is O;

$R^7$ is selected from the group: OH and $NH_2$; and $R^{15}$ is selected from the group: H and F.

In a most preferred embodiment, the compound of Formula (I) is: 3-[4-[1-(4-fluorophenyl)-2-phenyl-but-1-enyl]phenyl] acrylic acid;

Another embodiment of the present invention provides a pharmaceutical composition, comprising: a pharmaceutically acceptable carrier and a therapeutically effective amount of a compound of Formula (I).

Another embodiment of the present invention provides a method of treating cancer and disease states, comprising: administering to a host in need of such treatment a therapeutically effective amount of a compound of Formula (I), or a pharmaceutically acceptable prodrug or salt form thereof.

DEFINITIONS

As used herein, the following terms and expressions have the indicated meanings. The compounds of the present invention may contain an asymmetrically substituted carbon atom, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are intended, unless the specific stereochemistry or isomer form is specifically indicated.

The term "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. In addition, the term is intended to include both unsubstituted and substituted alkyl groups, the latter referring to alkyl moieties having one or more hydrogen substituents replaced by, but not limited to halogen, hydroxyl, carbonyl, alkoxy, ester, ether, cyano, phosphoryl, amino, imino, amido, sulfhydryl, alkylthio, thioester, sulfonyl, nitro, heterocyclo, aryl or heteroaryl. It will also be understood by those skilled in the art that the substituted moieties themselves can be substituted as well when appropriate. The term "haloalkyl" as used herein refers to an alkyl substituted with one or more halogens.

The terms "halo" or "halogen" as used herein refer to fluoro, chloro, bromo and iodo. The term "aryl" is intended to mean an aromatic moiety containing the specified number of carbon atoms, such as, but not limited to phenyl, indanyl or naphthyl.

As used herein, the terms "cycloalkyl" "bicycloalkyl" "carbocycle" or "carbocyclic residue" are intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7- membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7- membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1 H-indazole, 2-pyrrolidonyl, 2 H,6 H-1,5,2-dithiazinyl, 2 H-pyrrolyl, 3 H-indolyl, 4-piperidonyl, 4aH-carbazole, 4 H-quinolizinyl, 6 H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2 H,6 H-1,5,2-dithiazinyl, dihydrofuro [2,3-b]tetrahydrofuran, furanyl, furazanyl, imidazolidinyl, imidazolinyl, imidazolyl, 1 H-indazolyl, indolenyl, indolinyl, indolizinyl, indolyl, isobenzofuranyl, isochromanyl, isoindolazyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4 H-quinolizinyl, quinoxalinyl, quinuclidinyl, carbolinyl, tetrahydrofuranyl, tetrahydroisoquinolinyl, tetrahydroquinolinyl, 6 H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1 H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The term "heteroaryl" as used herein refers to a 5-membered or 6-membered heterocyclic aromatic group that can optionally carry a fused benzene ring and that can be unsubstituted or substituted.

The terms "linear and cyclic heteroalkyl" are defined in accordance with the term "alkyl" with the suitable replacement of carbon atoms with some other atom such as nitrogen or sulfur which would render a chemically stable species.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, meglumine, lysine, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th ed., Mack Publishing Company, Easton, Pa., 1990, p. 1445, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs", as the term is used herein, are intended to include any covalently bonded carriers which release an active parent drug of the present invention in vivo when such prodrug is administered to a mammalian subject. Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfydryl group, respectively. Examples of prodrugs include, but are not limited to, acetate, formate, and benzoate derivatives of alcohol and amine functional groups in the compounds of the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, the term "anti cancer" or "antiproliferative" agent includes, but is not limited to, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, etoposide, teniposide, vinblastine, vincristine, vinorelbine, procarbazine, asparaginase, pegaspargase, octreotide, estramustine, hydroxyurea. THF is an abbreviation for tetrahydrofuran; DME is an abbreviation for ethylene glycol dimethyl ether.

DOSAGE AND FORMULATION

The selective estrogen receptor modulator compounds of this invention can be administered as treatment for or prevention of cancer or other disease states by any means that produces contact of the active agent with the agent's site of action in the body of a mammal. They can be administered by any conventional means available for use in conjunction with pharmaceuticals, either as individual therapeutic agents, in combination with other compounds of formula I, or, with other therapeutic agents, such as anticancer or anti-proliferative agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. The skilled artisan will appreciate that well known excipients and pharmaceutical carriers are described in Remington's Pharmaceutical Sciences, 18th ed., Mack Publishing Company, Easton, Pa., 1990, a standard reference text in this field, the disclosure of which is hereby incorporated by reference.

SYNTHESIS

The compounds of the present invention can be synthesized using the methods described below, together with synthetic methods known in the art of synthetic organic chemistry, or variations thereon as appreciated by those skilled in the art. Preferred methods include, but are not limited to, those methods described below. Each of the references cited below are hereby incorporated herein by reference.

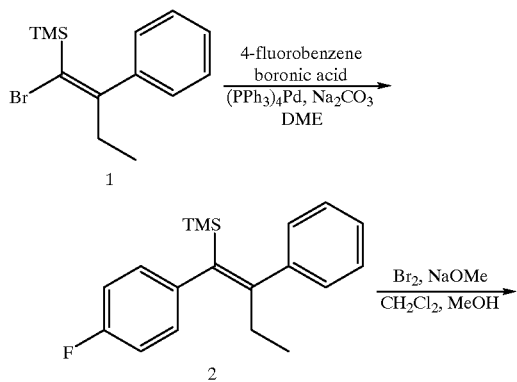

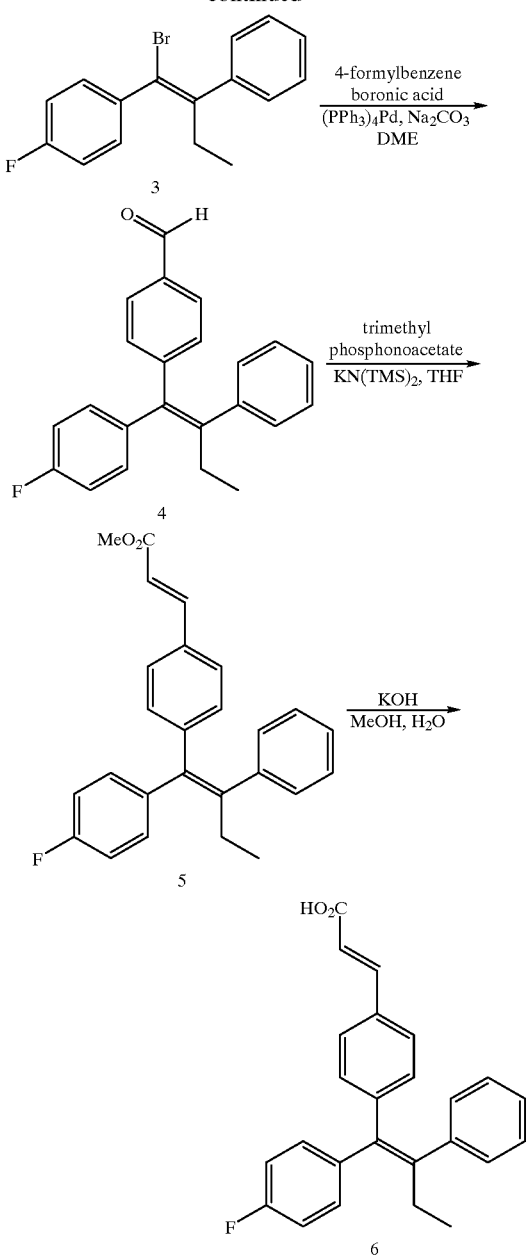

(Z)-1-(4-fluorophenyl)-2-phenyl-1-(trimethylsilyl)-1-butene (2). To a solution of (E)-1-bromo-2-phenyl-1-(trimethylsilyl)-1-butene (Miller R. B., Al-Hassam, M. I. J. Org. Chem. 1985, 50, 2121–2123) (1) (4.4 g, 15.5 mmol) in DME (50 mL) was added 4-fluorobenzene boronic acid (2.63 g, 18.9 mmol), tetrakis(triphenylphosphine)palladium (0) (1.0 g, 0.9 mmol), and 2N aqueous sodium carbonate(9.5 mL, 19 mmol). After refluxing overnight the solvent was removed under reduced pressure and the residue was chromatographed (silica gel, hexanes) to give (2) as a white solid (4.2 g, 91%): [1] H NMR (CDCl$_3$) δ 7.30 (m, 3 H), 7.19 (m, 2 H), 7.00 (m, 4 H), 2.12 (q, J=7.7 Hz, 2 H), 0.72 (t, J=7.7 Hz, 3 H), –0.35 (s, 9 H).

(Z)-1-Bromo-1-(4-fluorophenyl)-2-phenyl-1-butene (3). To a solution of (2) (3.93 g, 13.2 mmol) in CH$_2$Cl$_2$ (25 mL) at –78° C. was added bromine (2.5 g, 15.8 mmol) in 11 mL CH$_2$Cl$_2$ dropwise over 0.5 h. A solution of NaOMe (26.2 mmol) in methanol (36 mL) was added and the mixture was allowed to warm to rt. After stirring 3.5 h, EtOAc was added and the solution was washed with water, brine, and was dried (MgSO$_4$). The solvent was removed under reduced pressure and the resulting solid was recrystallized (methanol) to give the bromide (3) as a white solid (2.36 g, 59%): $^1$H NMR (CDCl$_3$) δ 7.33 (m, 7 H), 7.08 (m, 2 H), 2.33 (q, J=7.7 Hz, 2 H), 0.86 (t, J=7.7 Hz, 3 H).

(E)-1-(4-formylphenyl)-1-(4-fluorophenyl)-2-phenyl-1-butene (4). To a solution of the bromide 3 (2.0 g, 6.54 mmol) in DME (30 mL) was added 4-formylbenzene boronic acid (1.37 g, 9.11 mmol), tetrakis(triphenylphosphine)palladium (0) (800 mg, 0.7 mmol), and 2N aqueous sodium carbonate (4.8 mL, 9.6 mmol). After refluxing overnight the solvent was removed under reduced pressure and the residue was chromatographed (silica gel, 5% EtOAc/hexanes) to give the aldehyde (4) as a white solid (2.0 g, 92%): $^1$H NMR (CDCl$_3$) δ 9.83 (m, 1 H), 7.52 (d, J=8.4 Hz, 2 H), 7.15 (m, 11 H), 2.49 (q, J=7.3 Hz, 2 H), 0.94 (t, J=7.3 Hz, 3 H); APcI m/z: 372 (M+H+CH$_3$CN$^+$, 100%).

Methyl 3-[4-[1-(4-fluorophenyl)-2-phenyl-but-1-enyl]phenyl]acrylate (5). To a solution of trimethyl phosphonoacetate (412 mg, 2.26 mmol) in THF (15 mL) at 0° C. was added 1M sodium bis(trimethylsilyl)amide in THF (2.26 mL, 2.26 mmol) dropwise. After stirring 15 min the mixture was cooled to −78° C. and a solution of aldehyde (4) (625 mg, 1.89 mmol) in THF (8 mL) was added dropwise. The solution was allowed to warm to rt. After stirring 4 h, brine was added and the mixture was extracted with EtOAc. The combined organic layers were washed with water, brine, and dried (MgSO$_4$). The solvent was removed under reduced pressure and the residue was chromatographed (silica gel, 7.5 to 15% EtOAc/hexanes) to give the ester (5) as a white solid (658 mg, 90%): $^1$H NMR (CDCl$_3$) δ 7.52 (d, J=16.1 Hz, 1 H), 7.15 (m, 11 H), 6.86 (d, J=8.1 Hz, 2 H), 6.28 (d, J=16.1 Hz, 1 H), 3.76 (s, 3 H), 2.47 (q, J=7.7 Hz, 2 H), 0.93 (t, J=7.7 Hz, 3 H); APcI m/z: 428 (M+H+CH$_3$CN$^+$, 100%).

3-[4-[1-(4-fluorophenyl)-2-phenyl-but-1-enyl]phenyl]acrylic acid (6). To a solution of ester (5) (300 mg, 0.78 mmol) in methanol (25 mL) and THF (8 mL) was added 1N KOH (12 mL, 12 mmol). After stirring overnight the solvent was partially removed under reduced pressure, the mixture was acidified with 1N HCl, and was extracted with EtOAc. The combined organic layers were washed with brine and were dried (MgSO$_4$). The solvent was removed under reduced pressure and the residue was chromatographed (silica gel, 5% methanol/CH$_2$Cl$_2$) to give the acid (6) as a white solid (270 mg, 93%): $^1$H NMR (CDCl$_3$) δ 7.60 (d, J=15.8 Hz, 1 H), 7.13 (m, 11 H), 6.87 (d, J=8.5 Hz, 2 H), 6.28 (d, J=15.8 Hz, 1 H), 2.47 (q, J=7.3 Hz, 2 H), 0.93 (t, J=7.3 Hz, 3 H); APcI m/z: 414 (M+H+CH$_3$CN$^+$, 100%).

UTILITY

The biological activity of the compounds of Formula (I) was evaluated according to the following protocols provided below.

Those skilled in the art will appreciate that several acceptable varieties of estrogen receptor binding assays are known and available for initial screening of the compounds of the present invention with respect to their ability to bind to the appropriate receptor.

Estrogen receptor binding

Estrogen receptor binding was determined using a competition assay and recombinant human estrogen receptor alpha. Receptor and 3 H-estradiol were incubated overnight in the presence or absence of inhibitor. Receptor bound 3 H-estradiol was determined at each inhibitor concentration by separating free from bound 3 H-estradiol using membrane filtration. The concentration to prevent 50% 3 H-estradiol binding was determined from the binding inhibition curves and the Kd calculated. Table 1 (below) shows the Kd values for compound (6), 3-[4-[1-(4-fluorophenyl)-2-phenyl-but-1-enyl]phenyl]acrylic acid.

Estrogen Receptor Binding

TABLE 1

| Kd values for 17b-estradiol and compound (6). | | |
|---|---|---|
| Compound | Ki | st. dev. |
| 17b-ESTRADIOL | 0.0062 | 0.002 |
| Compound (6) | 0.4290 | 0.066 |

Cell growth inhibition

The hormone dependent human breast cancer cell line, MCF-7, was grown in 96-well dishes. Titration of the SERM was added (10-4-10-12M) either in the presence or absence of estrogen. Growth was monitored by sulforhodamine B staining as an index of cell number (SRB; Skehan P, Storeng R, Scudiero D, et al. New calorimetric cytotoxicity assay for anticancer drug screening. J. Natl Cancer Inst 1990; 82:1107–12) The concentration of SERM needed to suppress cell growth by 50% was determined from the drug dose-response titration curves.

Uterine Wet Weight Inhibition

Ovariectomized female mice were administered either saline or saline containing 0.32 ug 17B-estradiol S.C. and labrofil or SERM in labrofil orally (0–50 mg/kg) on days 1, 2, and 3. On day 4 mice were euthanized and uteri carefully dissected. Following blotting the uterine wet weights were determined. Agents were compared for the ability to suppress estrogen stimulated uterine growth and the ability to stimulate uterine growth when administered alone. FIG. 1 shows a dose-related inhibition of estrogen stimulated mouse uterine weight.

MCF-7 or MCF-7 Tamoxifen Dependent Tumor Growth

MCF-7 tumors were grown in athymic mice with estrogen supplementation (Robinson S. P. and Jordan V. C., Cancer Res. 49 1758–62 1989). The day of tumor implant was designated as day 0. SERM therapy was administered as either a continuous release preparation implanted sc or by frequent dosing (sc, ip or po). Tumor growth was monitored by caliper measurements and converted to volume by the formula:

Volume=width2×length.

Blood Lipids

Cholesterol and blood lipids were determined according to Kauffman et al (JPET 280:146–153 1997). Mature (60–90) days old Sprague Dawley rats were ovariectomized and treated daily for 4–7 days with the SERM. Following cardiac bleeds circulating cholesterol, HDL and triglycerides were measured using commercial assays.

Bone Mineral Density Studies

Mature Sprague-Dawley rats were either ovariectomized or sham operated. Animals were treated daily with either SERM or estrogen for 4 to 6 weeks. Bone density was determined by Dual energy X-ray absorption as previously described (J.Med Chem 1994 37 1550–1552).

What is claimed is:

1. A compound according to Formula (I):

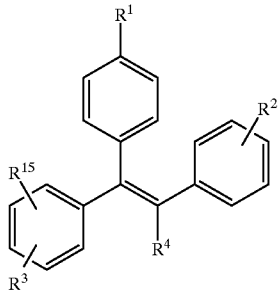

Formula (I)

or a stereoisomer or pharmaceutically acceptable salt form thereof, wherein:

$R^1$ is $(CH_2)_n CR^5 = CR^6 R^7$;

$R^2$ is H;

$R^3$ is selected from the group: F, Cl, BR, and I;

$R^4$ is selected from the group: CN, $NO_2$, $CH_3$, $CH_2CH_3$, $CH_2CH_2Y$ and Y;

$R^5$ and $R^6$ are independently at each occurrence selected from the group: H, O, OH, $C_{1-4}$ alkyl, $C_{2-4}$ alkenyl, $C_{2-4}$ alkynyl, $XC_{1-3}$ alkyl, $XC_{2-4}$ alkenyl, $XC_{2-4}$ alkynyl and Y;

$R^7$ is independently at each occurrence selected from the group: $NH_2$, CN, O, OH, $C_{1-4}$ alkyl-OH, $C(O)O(CH_3)$, $C(O)NR^{10}R^{11}$, $C(O)NR^{12}R^{13}$, $C_{1-4}$ alkyl-$NR^{10}R^{11}$, $C(O)R^{12}$, $C(O)OR^{12}$, $C(O)NR^{12}OR^{13}$, $C(O)NHC(O)R^{12}$, $C(O)NHCH_2R^{12}$, C($NH_2$) ($NOR^{12}$), $S(O)R^{12}$, $S(O)(O)(OR^{12})$, $S(O)(O)(NHCO_2R^{12})$, $PO_3R^{12}$, $P(O)(NR^{12}R^{13})(NR^{12}R^{13})$, $P(O)(NR^{12}R^{13})(OR^{14})$, $CONR^{12}(CH_2)_q OCH_3$, $CONR^{12}(CH_2)_q NR^8 R^9$, and oxadiazole substituted with $CH_3$;

$R^8$ and $R^9$ are independently at each occurrence selected from the group: $C_{1-7}$ alkyl, $C_{3-7}$ cycloalkyl, $O—C_{1-7}$ alkyl, $C_{1-7}$ alkyl-Y, and phenyl;

$R^{10}$ and $R^{11}$ are independently $CH_3$ or $C_2H_5$, or taken together form a morpholino group bonded via its nitrogen atom;

$R^{12}$ and $R^{13}$ and $R^{14}$ are independently at each occurrence selected from the group: H, $C_{1-2}$ alkyl, $C_{2-12}$ alkenyl, $C_{2-12}$ alkynyl, $O—C_{1-2}$ alkyl, $O—C_{2-12}$ alkenyl, $O—C_{2-12}$ alkynyl, $C_{3-7}$ cycloalkyl, $C_{3-7}$ cycloalkenyl, linear and cyclic heteroalkyl, aryl, heteroaryl, and Y;

$R^{15}$ is selected from the group: H and F;

X is selected from the group: O and S;

Y is selected from the group: F, Cl, Br, and I;

n is selected from: 0, 1, and 2;

m is selected from: 1 and 2;

p is selected from: 1, 2, 3, and 4; and q is selected from: 1, 2, 3, 4, 5, 6, 7, 8, 9, 10, 11, and 12.

2. A compound according to claim 1, wherein:

$R^1$ is $(CH_2)_n CR^5 = CR^6 R^7$;

$R^2$ is H;

$R^3$ is F;

$R^4$ is $CH_3$;

$R^5$ is H;

$R^6$ is O; and $R^{15}$ is selected from the group: H and F.

3. A compound according to claim 1, wherein:

$R^1$ is $CR^5 \uparrow CR^6 R^7$ $R^2$ is H;

$R^3$ is F;

$R^4$ is $CH_3$;

$R^5$ is H;

$R^6$ is O;

$R^7$ is selected from the group: OH and $NH_2$; and $R^{15}$ is selected from the group: H and F.

4. A compound according to claim 1, wherein the compound is selected from:

(a) 3-[4-[1-(4-fluorophenyl)-2-phenyl-but-1-enyl]phenyl] acrylic acid.

5. A pharmaceutical composition, comprising: a pharmaceutically acceptable carrier and a therapeutically effective amount of a compound of any one of claims 1 through 4.

6. A method of treating of breast, uterine, ovarian, prostrate and colon cancer, osteoporosis, cardiovascular disease, and benign proliferative disorders, comprising: administering to a host in need of such treatment a therapeutically effective amount of a compound of any one of claims 1 through 4, or a pharmaceutically acceptable salt form thereof.

* * * * *

UNITED STATES PATENT AND TRADEMARK OFFICE
CERTIFICATE OF CORRECTION

PATENT NO.    : 6,528,681 B2
DATED         : March 4, 2003
INVENTOR(S)   : Robert F. Kaltenbach and George L. Trainor It is certified that error appears in the above-identified patent and that said Letters Patent is hereby corrected as shown below:

Column 16,
Line 23, should read -- $R^1$ is $CR^5 = CR^6R^7$ --

Signed and Sealed this

Second Day of September, 2003

JAMES E. ROGAN
*Director of the United States Patent and Trademark Office*